United States Patent [19]
Ripich et al.

[11] Patent Number: 5,893,860
[45] Date of Patent: Apr. 13, 1999

[54] TONGUE SCRAPER

[76] Inventors: Robert J. Ripich, 2622 Glenmont Rd.; James Bower, 2810 Brentwood Close, both of NW Canton, Ohio 44708

[21] Appl. No.: 09/009,698

[22] Filed: Jan. 20, 1998

Related U.S. Application Data

[60] Provisional application No.60/040,608, Mar. 17, 1997.

[51] Int. Cl.⁶ .................................................. A61B 17/24
[52] U.S. Cl. ................................................................ 606/161
[58] Field of Search ................................ 606/161, 160, 606/1; 15/111, 110, 167.1, 160; 132/309; D24/147, 176, 152

[56] References Cited

U.S. PATENT DOCUMENTS

| | | |
|---|---|---|
| D. 242,744 | 12/1976 | Rendleman et al. |
| D. 264,878 | 6/1982 | Kitzis . |
| D. 265,506 | 7/1982 | Finamore . |
| D. 291,001 | 7/1987 | Gaskins . |
| D. 295,343 | 4/1988 | Regalado . |
| D. 295,695 | 5/1988 | Golzari . |
| D. 301,372 | 5/1989 | Tsen . |
| D. 303,426 | 9/1989 | Simonian . |
| D. 324,912 | 3/1992 | Hansen . |
| D. 360,262 | 7/1995 | Ly . |
| D. 365,395 | 12/1995 | Miyauchi . |
| D. 367,707 | 3/1996 | Baker . |
| 619,466 | 2/1899 | Buchmann ............... 606/161 |
| 781,292 | 1/1905 | Murphree ............... 606/161 |
| 856,711 | 6/1907 | Lees ............... 606/161 |
| 1,811,775 | 6/1931 | Barkwill ............... 606/161 |
| 3,502,082 | 3/1970 | Chatfield ............... 606/161 |
| 4,455,704 | 6/1984 | Williams . |
| 4,488,327 | 12/1984 | Snider . |
| 4,582,059 | 4/1986 | Tiwari . |
| 4,875,496 | 10/1989 | Prabhudass . |
| 5,061,272 | 10/1991 | Reese . |
| 5,217,475 | 6/1993 | Kuber . |
| 5,226,197 | 7/1993 | Nack et al. . |
| 5,282,814 | 2/1994 | Srivastava . |
| 5,530,981 | 7/1996 | Chen . |
| 5,569,278 | 10/1996 | Persad . |
| 5,827,308 | 10/1998 | Thakur et al. ............... 606/161 |

*Primary Examiner*—Michael Buiz
*Assistant Examiner*—Vikki Trinh
*Attorney, Agent, or Firm*—Sand & Sebolt

[57] ABSTRACT

An improved tongue scraper or oral hygiene tool is designed to most effectively and harmlessly remove plaque, tartar, bacteria, dead tissue, food debris, etc. from the tongue. The tool is made of a nonporous substance capable of withstanding high temperatures during repeated sterilization such as metal, and preferably stainless steel. The tool includes unique curves and smooth edges designed to define a working edge contoured similar to that of the tongue and having a nongagging and self-cleaning profile and size.

9 Claims, 1 Drawing Sheet

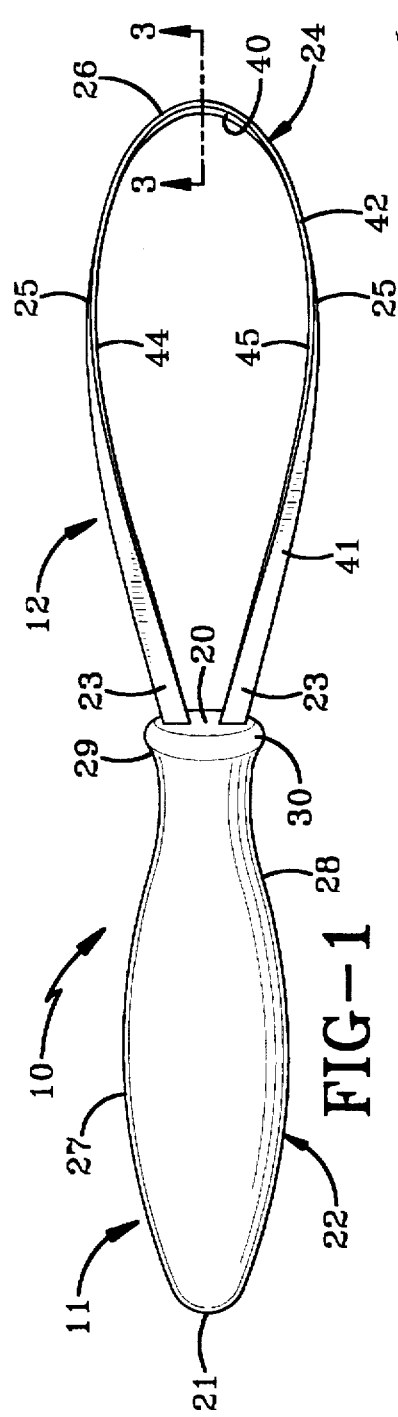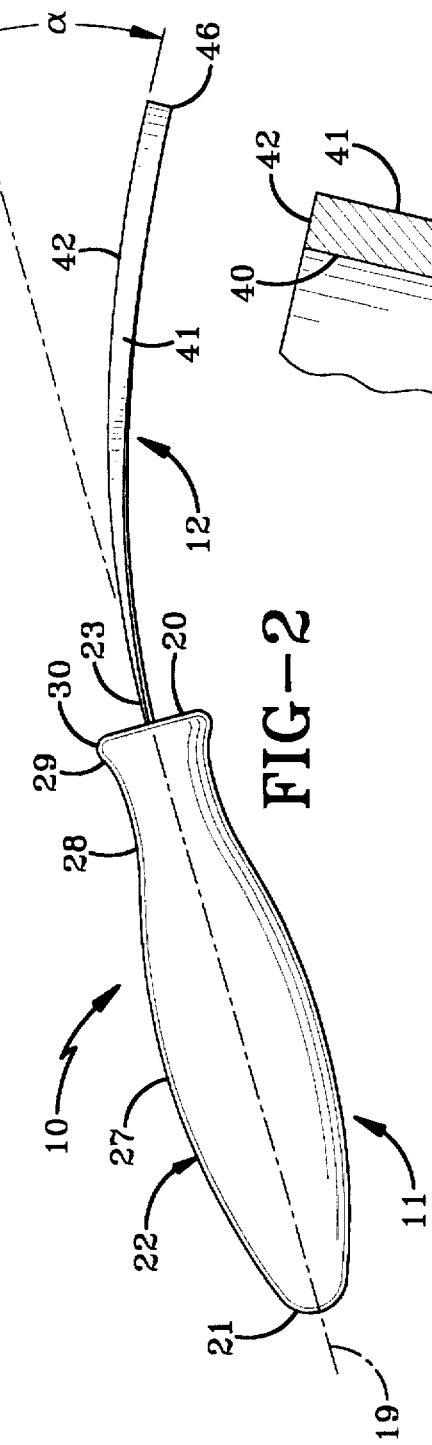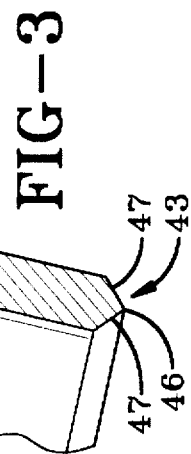

1
TONGUE SCRAPER

CROSS REFERENCE

A related patent application was filed in the United States on Sep. 29, 1997 as Ser. No. 08/940,146 claiming priority to U.S. Provisional patent application No. 60,040,608 filed on Mar. 17, 1997 of which the content of both is hereby incorporated by reference.

BACKGROUND OF THE INVENTION

1. Technical Field

The invention relates to tongue cleaning devices. More particularly, the invention relates to devices designed and used for removal of plaque, tartar, bacteria, food debris, and dead tissue from the tongue since buildup of plaque, tartar, bacteria, and food debris may result in halitosis or bad breath, tooth decay, and gum disease. Specifically, the invention is a reusable tongue scraping device of a unique design, shape and configuration so as to be reusably sterilizable, self-cleaning and easily rinsed, nongagging, tongue-fitting, and nonthreatening while effectively and harmlessly removing plaque, tartar, bacteria, food debris, dead tissue, and other microorganisms from the tongue thereby reducing or eliminating halitosis or bad breath, tooth decay, and gum and other periodontal diseases.

2. Background Information

It is well known that plague, tartar, bacteria, food debris, dead tissue, and other debris and microorganisms live and/or accumulate within the mouth and throat, including on the teeth and tongue. For this reason, most people brush their teeth one or more times per day so as to attempt to remove at least some of this particulate. In addition, it is also common practice for most people to floss between their teeth as well as gargle or rinse their mouth out with various mouth rinses and mouth washes for the same or similar reasons. Most individuals further regularly see a dentist or other oral/dental hygiene provider during which the teeth are cleaned, although this is generally accomplished no more often than twice per year. These basic forms of oral hygiene are widely accepted in the civilized world.

Furthermore, many people use gum, breath mints, and other products to freshen their mouth and thus their breath. These gum and mints are only short term ways of covering up the problem, that is the accumulation of the above-mentioned materials within the mouth, and therefore the above-mentioned processes of brushing and flossing are still required.

However, these processes of brushing and flossing teeth, as well as gargling and/or rinsing of the mouth with various rinses and mouth washes, are not always successful, or are sometimes only partially successful, in removing all of the plaque, tartar, bacteria, food debris, and dead tissue from the entire mouth cavity, and particularly the tongue since much of the focus is on the teeth. This focus by these well-known oral hygiene processes is well founded for tooth decay prevention, but is only a part of general mouth and throat hygiene since the buildup of plaque, tartar, bacteria, and food debris on the tongue may result in halitosis or bad breath, tooth decay, and gum disease. All of which have serious medical and/or social effects.

It has recently been discovered that halitosis or bad breath is a result of the buildup of the plaque, tartar, food debris, bacteria, dead tissue, and other microorganisms, either dead or alive, within the mouth cavity, and particularly on the tongue since the teeth are generally brushed regularly. In addition, it has been found that during sleep, the tongue often becomes coated with a film or coating having an offensive odor. Furthermore, during sleep and at other times of the day, saliva, mucus, sinus drainage, and other materials often dry on the tongue providing additional buildup. Finally, various bacteria and viruses also may buildup on the tongue when one is ill. All of this buildup is undesirable since the tongue, although generally smooth in nature, includes projections, grooves, and other minute crevices in which bacteria, germs, etc. can accumulate and grow causing mouth odors. Coupled with this is the transformation of the various buildup including these bacteria and germs as well as food debris, dead cells, and other microorganisms into plaque and tartar when mixed with saliva. It is well-known that this plaque is a source of offensive mouth odors. The soft, yet flexible nature of the tongue when coupled with the above-described uneven yet generally smooth terrain thereof, supplies the plaque with sufficient surface area to relatively permanently affix itself to, absent a scraping or similar removal process.

In the past, cleaning of the tongue has often been overlooked, or alternatively has been primitively attempted using the brushes on a conventional toothbrush. The toothbrush, however, is not well suited for this purpose since the bristles of the toothbrush are often too soft and flexible to remove the hard buildup described above. In addition, the overall size, shape and configuration of the toothbrush makes the toothbrush not well suited for the removal of this buildup from the tongue.

As a result, it was discovered that tongue cleaning devices specifically designed solely for use as tongue scrapers could possibly better clean off the above-mentioned buildup including the plaque, tartar, bacteria, food debris, and dead tissue that results in halitosis or bad breath, tooth decay, and gum disease. Prior examples of such tongue cleaning devices are shown in U.S. Utility Pat. Nos. 4,445,704, 4,488,327, 4,582,059, 4,875,496, 5,061,272, 5,217,475, 5,226,197, 5,282,814, 5,569,278, as well as U.S. Design Pat. Nos. D242,744, D246,878, D265,506, D291,001, D295,343, D295,695, D301,372, D303,426, D324,912, D360,262, D365,395, and D367,707.

Although many of these prior art tongue cleaning devices were satisfactory for their intended purpose of cleaning at least some of the buildup from the tongue, several disadvantages or problems exist in the design and use of these, and therefore an improved tongue scraper design is needed. These disadvantages and problems include:

(1) an inability to sterilize the tongue scraper at all, repeatedly, or at sufficiently high temperatures such as those encountered in either professional disinfecting machinery or home dishwashers, due to the plastic or soft/thin metal construction of the tongue scraper;

(2) a porous finish in which germs, bacteria, microorganisms, and other microbial material may collect, breed, grow, etc.;

(3) a brittle or otherwise nondurable construction, such as plastic, which is not sufficiently tough and durable to withstand both use and misuse;

(4) a construction capable of being marred, scratched, dented, fractured, or otherwise physically damaged, particularly by rough handling, thereby making the tongue cleaning device ineffective;

(5) a nonrigid construction which bends or otherwise gives too much during use, and/or a construction such as of plastic that does not maintain its rigidity over time;

(6) a configuration that is not contoured similar to the shape of the tongue;

(7) a size that is not similar to the size of the tongue;

(8) a shape that is not similar to the shape of the tongue;

(9) a working edge that does not remain in contact with the tongue surface throughout the entire cleaning process;

(10) a design which causes gagging;

(11) a design with grooves, crevices, or other spots that promote buildup within the device which is undesirable;

(12) a design that prohibits proper rinsing of the device thereby promoting buildup on the device;

(13) a handle design that is not ergonomic;

(14) a handle that is not of sufficient strength and rigidity as is needed during the cleaning process;

(15) a handle that is not user friendly;

(16) a handle that is not designed to allow for easy and controlled insertion of the tongue scraper into a human mouth and into proper position on the tongue, particularly the most posterior portion of the tongue;

(17) an overall design that does not provide access to the most posterior portion of the tongue where the greatest concentration of plaque buildup occurs;

(18) a working edge design that clogs;

(19) a working edge design that does not sufficiently penetrate the tongue papillae;

(20) a working edge or other surface that is hazardous and/or threatening due to sharp edges;

(21) a design too flimsy resulting in a lack of control during use;

(22) a size, shape, and design that is too short thereby increasing the risk of accidental swallowing or lodgement within the throat; and

(23) a design that includes moving joints, fasteners, or other needless constructions that provide for more difficult and less effective use, as well as a device that is more expensive, less reliable, and more susceptible to breakage.

SUMMARY OF THE INVENTION

These and other disadvantages and problems have resulted in the Applicant's realization that a new device is needed to address and solve some and/or all of the above disadvantages and problems. This new device encompasses the following and other objectives and advantages.

Objectives of the invention include providing an improved oral hygiene device.

Another objective of the invention is to provide an improved tongue cleaning device.

Another objective of the invention is to provide an improved tongue-scraping device.

Another objective of the invention is to provide such an improved oral-hygiene device, tongue cleaning device, and/ or tongue scraper that is replete of the disadvantages of the prior art devices including those disadvantages listed above.

Another objective of the invention is to provide an oral hygiene device, tongue cleaner and/or tongue scraper for removing plaque, tartar, food debris, bacteria, etc. from the surface of the tongue, and more particularly from the plurality of grooves, crevices, and other contours within the tongue and off of the papillae of the tongue, specifically in and around the fungiform and filiform papillae toward the base or dorsal surface of the tongue.

Another objective of the invention is to provide an oral hygiene device, tongue cleaner, and/or tongue scraper for eliminating or reducing mouth odors caused by plaque and other material buildup on the tongue.

Another objective of the invention is to provide an oral hygiene device, tongue cleaner, and/or tongue scraper that improves the taste of food by removing plaque and other material buildup from the tongue, and specifically from the taste buds on the tongue surface.

Another objective of the invention is to provide an oral hygiene device, tongue cleaner, and/or tongue scraper having a unique size, shape, configuration and design so as to maintain maximum contact with the tongue surface during use.

Another objective of the invention is to provide an oral hygiene device, tongue cleaner, and/or tongue scraper having a configuration similar to the shape of the tongue, that is of a contour similar to the curved shape of the tongue from its posterior connection in the throat to its anterior tip.

Another objective of the invention is to provide an oral hygiene device, tongue cleaner, and/or tongue scraper having a size that is similar to the size of the tongue, particularly the long sweeping curve of the tongue from its posterior connection in the throat to its anterior tip.

Another objective of the invention is to provide an oral hygiene device, tongue cleaner, and/or tongue scraper having a mouth insertion portion of a shape that is similar to the shape of the tongue which is longer from its posterior end to its anterior tip than it is wide.

Another objective of the invention is to provide an oral hygiene device, tongue cleaner, and/or tongue scraper having a working edge that remains in contact with the tongue surface throughout the cleaning process.

Another objective of the invention is to provide an oral hygiene device, tongue cleaner, and/or tongue scraper that is replete of grooves, crevices, or other spots that promote buildup of the scraped plaque, etc. within the device, which is undesirable.

Another objective of the invention is to provide an oral hygiene device, tongue cleaner, and/or tongue scraper that is designed to allow for rinsing of the device thereby eliminating buildup on the device.

Another objective of the invention is to provide an oral hygiene device, tongue cleaner, and/or tongue scraper that is designed to not include rivets, fasteners, or other joints and connectors that are susceptible to buildup of the scraped plaque, etc., and in the event of the breaking of the device could be swallowed or otherwise cause choking.

Another objective of the invention is to provide an oral hygiene device, tongue cleaner, and/or tongue scraper that is designed in a manner not too likely to elicit gagging, that is the gag reflex, during use which would preclude proper cleaning.

Another objective of the invention is to provide an oral hygiene device, tongue cleaner, and/or tongue scraper that is replete of sharp or otherwise tissue damaging edges or surfaces that could injure the tongue or other surfaces in the mouth or throat.

Another objective of the invention is to provide an oral hygiene device, tongue cleaner, and/or tongue scraper that is ergonomic.

Another objective of the invention is to provide an oral hygiene device, tongue cleaner, and/or tongue scraper having a handle that comfortably fits the hand of a standard user.

Another objective of the invention is to provide an oral hygiene device, tongue cleaner, and/or tongue scraper having a handle that secures the two ends of the cleaning or scraping blade therein in a sanitary and easy to clean manner without grooves or fasteners.

Another objective of the invention is to provide an oral hygiene device, tongue cleaner, and/or tongue scraper having a handle design that is ergonomic.

Another objective of the invention is to provide an oral hygiene device, tongue cleaner, and/or tongue scraper having a handle that is of sufficient strength and rigidity as is needed during the cleaning process.

Another objective of the invention is to provide an oral hygiene device, tongue cleaner, and/or tongue scraper that is constructed so as to be capable of repeated sterilization at very high temperatures such as those encountered in either professional disinfecting machinery or home dishwashers without any damage to the invention.

Another objective of the invention is to provide an oral hygiene device, tongue cleaner, and/or tongue scraper with a nonporous surface that is replete of pores in which germs, bacteria, microorganisms, and other microbial material may collect, breed, grow, etc.

Another objective of the invention is to provide an oral hygiene device, tongue cleaner, and/or tongue scraper of a durable construction that is sufficiently tough and durable to withstand both use and misuse.

Another objective of the invention is to provide an oral hygiene device, tongue cleaner, and/or tongue scraper of a construction resistant to marring, scratching, denting, fracturing, or otherwise physical damage, particularly by rough handling, since these surface or edge occlusions would make the tongue cleaning device ineffective.

Another objective of the invention is to provide an oral hygiene device, tongue cleaner, and/or tongue scraper of a rigid construction which resists bending yet is not so brittle as to break when a bending force is applied thereto.

Another objective of the invention is to provide an oral hygiene device, tongue cleaner, and/or tongue scraper having a design that allows the user to gain access to the most posterior portion of the tongue where the greatest concentration of plaque buildup occurs.

Another objective of the invention is to provide an oral hygiene device, tongue cleaner, and/or tongue scraper having a working edge design that reduces or eliminates clogs.

Another objective of the invention is to provide an oral hygiene device, tongue cleaner, and/or tongue scraper having a working edge design that allows for sufficient penetration of the tongue papillae.

Another objective of the invention is to provide an oral hygiene device, tongue cleaner, and/or tongue scraper having a working edge or other surface that is not hazardous and/or threatening due to sharp edges.

Another objective of the invention is to provide an oral hygiene device, tongue cleaner, and/or tongue scraper having a design of sufficient rigidity thereby providing sufficient control during use.

Another objective of the invention is to provide an oral hygiene device, tongue cleaner, and/or tongue scraper that is of a size, shape, and design that is long enough to decrease the risk of accidental swallowing or lodgement within the throat.

Another objective of the invention is to provide an oral hygiene device, tongue cleaner, and/or tongue scraper having a design replete of moving joints, fasteners, or other needless constructions, thus providing for easier and more effective use, as well as a device that is less expensive, more reliable, and less susceptible to breakage.

Another objective of the invention is to provide an oral hygiene device, tongue cleaner, and/or tongue scraper that is easily, effectively, and efficiently manufactured and marketed.

Another objective of the invention is to provide an oral hygiene device, tongue cleaner, and/or tongue scraper that is simplified and inexpensive to manufacture and market.

Another objective of the invention is to provide a tongue cleaning device that meets all of the above-mentioned objectives.

These and other objectives and advantages are achieved by the improved tongue scraper, the general nature of which may be stated as a device with an elongated, molded and unitary handle having a central axis, and a body including a blade having a pair of ends and a mid-portion with a curve such that the ends are proximate each other, the mid-portion defined by a pair of opposing surfaces on the blade, the ends each being molded within the handle in a substantially planar manner with each other while the mid-portion of the blade includes a twist such that the opposing surfaces are nonplanar with the ends as molded in the handle.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

FIG. 1 is a perspective view of the tongue scraper invention;

FIG. 2 is a side view of the tongue scraper of FIG. 1; and

FIG. 3 is a sectional view of the blade taken along line 3—3 in FIG. 1.

Similar numerals refer to similar parts throughout the drawings.

DETAILED DESCRIPTION OF THE PREFERRED EMBODIMENTS

The improved tongue scraper is indicated as 10 and shown in FIGS. 1-2. The tongue scraper 10 including a handle 11 and a body 12. Handle 11 is an elongated structure with a central axis 19 (FIG. 2), the structure having a proximate end 20, a distal end 21 and a radially uniform exterior surface 22 therebetween. Body 12 is a twisted and planar member having a pair of ends 23 with a central portion 24 therebetween and including long, sweepingly curved sections 25 separated by curved end 26.

Proximate end 20 of handle 11 is a body receiving surface that in the displayed embodiment is a flat or substantially flat surface receiving both ends 23 of the body 12. The surface 20 is a transverse surface to the central axis 19, and in the displayed embodiment is a perpendicular or substantially perpendicular surface to the central axis 19. Proximate end 20 receives and securely holds body 12 to the handle 11.

Distal end 21 of handle 11 is a rounded or contoured end. This rounded or contoured end 21 provides a smooth, safe, and ergonomic termination to the handle 11.

The radially uniform exterior surface 22, extending between the ends 20 and 21, is similarly contoured for smooth, safe, and ergonomic feel. Specifically, the exterior surface 22 includes a smoothly curved body 27 of a uniform cross section taken at any perpendicular plane to the central axis 19, a narrow neck 28 also of a uniform cross section when taken at any perpendicular plane to the central axis, and an outwardly tapered or bell-shaped base 29 with a rounded lip 30 over to the proximate end 20. As best shown in FIGS. 1-2, the smoothly curved body 27 specifically includes a surface smoothly transitioning from distal end 21 in an increasing diametrical manner to a curved body mid point where the surface then decreases diametrically to a smooth transition into the narrow neck 28. The narrow neck 28 similarly but inversely tapers; specifically, the narrow neck 28 transitions smoothly from the exterior surface 22 in a decreasing diametrical manner to a neck mid point where the neck then increases diametrically to rounded lip 30. Rounded lip 30 smoothly transitions the narrow neck 28 of increasing diameter at that point into the base 29 which is substantially perpendicular to the central axis.

In accordance with one of the features of the invention, the twisted and planar body 12 includes the pair of ends 23 with the central portion 24 therebetween whereby the central portion 24 includes the pair of long, sweepingly curved sections 25 separated in approximately the middle by the curved end 26. In the displayed embodiment, the general shape of the body 12 is similar to that of a human tongue which is an elongated member with a slight curve from front to back. This curve is mimicked by the body 12 as best shown in FIG. 2 where the body curves away from the axis 19 in a smooth manner to an angle thereby defining a slight concave portion 31 between the ends 23 and the end 26. The elongated shape of the human tongue is mimicked by the body 12 as best shown in FIG. 1 where the body is of a generally tear drop, or skinny tear drop, shape except the ends 23 do not touch.

In more detail and in accordance with the main features of the invention, the twisted and planar body 12 is an elongated piece of a flat and planar material, such as a metal strip where the piece has two opposing rectangular faces 40 and 41, two opposing thin sides 42 and 43, and two opposing ends (not shown as each is molded within the handle 11). The elongated piece is initially straight, whereby this piece is twisted and bent to form the body 12 of the tongue scraper 10. The piece is bent about its mid portion to form the curved end 26. The piece is twisted about an axis axially through the elongated piece as shown by twists 44 and 45 to properly position and angle the scraping surface, which is thin side 43 as shown in FIGS. 1–3. This twist smoothly occurs from ends 23 to curve 26 as the body 12 at ends 23 is axially aligned and planar with axis 19 while the body 12 at curve 26 defines a plane that is transverse to the axis 19. This plane is not perpendicular to axis 19 as the piece further includes an overall arcing from ends 23 to curve 26 as defined by angle α.

In accordance with another feature of the present invention, the scraping surface or thin side 43 includes a scraping edge 46 as defined by angular faces 47 of the thin side 43 which angle to a sharp or well defined line, the scraping edge 46. The scraping edge 46 is preferably finished to provide a better surface scraping edge such as a sharp edge as shown in the displayed embodiment in FIG. 3. The scraping edge may alternatively be of a differing construction so long as it provides a scraping edge that removes the germs, bacteria, microorganisms, food, dead cells, microorganisms, and other microbial material may collect, breed, grow, etc. and in some cases turn into plaque and tartar when mixed with saliva while not scraping, cutting or otherwise damaging the tongue or mouth surfaces.

This scraping edge is shown as a sharp or well defined edge with a smooth, rounded, or otherwise finished edge in the FIGS. 1–3, although it may alternatively be of a jagged, toothed, serrated, grooved, notched, stepped, or otherwise patterned or uneven construction including triangular and square toothed designs.

The body 12 is made of any material sufficient to withstand the usage requirements while also being sterilizable. One such material is stainless steel which can be sterilized under intense heat in a repetitive nature without any damage to the device. The stainless steel has a nonporous finish so as to not allow organic material to collect on the device. The stainless steel construction allows the working edges, that is the scraping surface and edge 46 and 47, to remain unworn as each has exceptional durability over time and use. This working edge is further not easily marred by rough handling. The stainless steel construction provides a rigid tool that is not flimsy, bendable, or otherwise flexible during use under pressure against the user's tongue.

The handle 11 is made of any smooth, easy to handle, and user friendly material that is ergonomically shapable as shown in the Figures. One such material is a polymer material which has a user friendly feel and is replete of any sharp edges or corners which could harm the inner surface of the mouth or harbor germs, buildup, etc. The polymer material is also easily molded into the desired shape. The polymer must be capable of repetitive intense heat during sterilization.

The design is further a self-cleaning configuration that allows the working edge blade to be rinsed without the possibility of debris collecting in any corners.

The design is further such that the handle length and shape are optimal for the fit of the natural contours of the thumb and palm of the hand while providing the optimal length to reach the most posterior regions of the tongue. The handle is also designed to provide the strength needed to support the body while maintaining a nongagging contour.

The design further lacks joints, fasteners, bulky welds, etc., which define small or large crevices, grooves, etc. in which debris can collect.

One such specific configuration of the tongue scraper 10 includes a handle 11 of approximately 2 to 5 inches in length from its outermost or distal end 21 to its innermost or proximate end 20. Similarly, the body 12 is of approximately 2 to 5 inches in length from ends 23 to curve 26, and is preferably approximately 4½ inches in length. The width of the body 12 is of approximately 1 to 2 inches in width from the most spaced apart portions of curved sections 25, and is preferably approximately 1¼ to 1½ inches in width. As to the blade or body 12 constraints, one specific configuration includes a blade height from side 42 to edge 46 of between approximately ⅛ to ¼ inch, with a blade width from face 40 to face 41 of less than ⅛ inch and preferably between ¹⁄₆₄ and ¹⁄₁₆ inch. The twist of the body 12 is such that the inner and outer face of curve 26 is angled at between 45° and 90° of the plane of the inner and outer faces of ends 23 as defined along axis 19 by either face 40 or 41 at ends 23 adjacent handle 11, and preferably at approximately 70° as metal strip has been twisted approximately 90° but also arced or bent 20° as defined by angle α such that the blade or body 12 takes on the look shown in FIGS. 1 and 2. The result is a "net effect" approximately 70° angle between the inner side 40 of the the blade or body 12 at curve 26 and the axis 19.

This embodiment has one or more of the following benefits, advantages, objectives, design features, and other attributes:

The blade or body is made of surgical quality stainless steel, which will not fracture.

Stainless steel will give the blade or body and its working or scraping edge an exceptional durability not found in plastic cleaning tools. In particular, the working edge is not easily marred by rough handling, a potentially hazardous problem associated with plastic tongue cleaning tools.

Stainless steel material allows tongue scraper to maintain functionally rigid properties indefinitely.

Properties of stainless steel allow for unlimited sterilization cycles.

Can be sterilized using a dishwasher or other professional disinfecting machinery.

Nonporous finish does not allow organic material to collect on surface.

Unique curves, twists, and arcs comprising the working or scraping edge designed to fit the muscle contours of the tongue most effectively as the tool is dragged with moderate pressure over its surface.

Unique dual sided working blade or body in which both central portion of tongue as well as the sides of tongue are cleaned.

Working or scraping edge is designed to be obtuse, or greater than 90 degrees to tongue surface, so debris can be lifted away during cleaning process.

Body is twisted and bent to optimally define the scraping edge.

Unequaled "nongagging" design achieved through an optimal curve, depth/height of the body and the slope or "depth" of the working edge in relation to where the handle begins.

A "self-cleaning" design allows for the working or scraping edge to be rinsed without the possibility of debris collecting in corners.

Properties of tool design and construction materials lend themselves to a variety of angles and curves. Thus, there is the ability to create an infinite amount of scale models for different oral hygiene cases (i.e. small/large mouths, nonsensitive/sensitive tongues).

Designed has the ability to be tailored for every possible customer, or in general standard sizes and shapes.

Unique curve of body provides a progressive pressure spectrum for placing optimum cleaning forces on the tongue.

Unique design of tool allows for infinite incremental changes of this pressure spectrum through changes in the severity of blade curve during construction.

The blade or body is molded within the handle for rigidity and for providing a handle and a handle-body connection replete of any corners, edges or other areas in which debris could collect.

Designed for easy one-handed use as compared to older two-handed designs.

Thickness of working edge optimized through use of 22-gauge steel (~0.029 in.)

Handle length and body angle, curve, twist, bend, and/or arc designed especially to fit the natural contours of the thumb and palm of the hand while providing the optimal length and design to reach the most posterior regions of the tongue where most bacteria are found as well as the sides of the tongue.

The handle construction and body angle is also designed to provide the strength needed to support the scraping edge blade while maintaining superb "nongagging" contours.

Overall tongue scraper design allows cleaning of most posterior portion of tongue that contains greatest concentration of filiform papillae and associated plaque buildup.

Sleek, aerodynamic design aids in the perception of the tongue scraper as a nonthreatening tool as opposed to other razor shaped, bulky designs.

Designed to be psychologically comforting by resembling common eating utensils.

The use of this unique tool reduces halitosis by decreasing the amount of plaque and organic food substrate that accumulates in and around fungiform and filiform papillae of the tongue. This reduces bacteria and sulphur byproducts that can cause halitosis, tooth decay, and gum disease.

Unique cleaning action of this tool on taste papillae results in improved taste sensation.

Completely rigid design allows complete control of tool in desired areas of tongue. This feature is not found in flimsy, plastic tongue cleaners.

The length of the tool and its inherent rigid properties make the tongue scraper substantially less likely to be swallowed or inhaled than other short, flimsy products.

Accordingly, the improved tongue scraper is simplified, provide effective, safe, inexpensive, and efficient devices which achieves all the enumerated objectives, provide for eliminating difficulties encountered with prior devices, and solve problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved tongue scraper is constructed and used, the characteristics of the construction, and the advantageous, new and useful results obtained; the new and useful structures, devices, elements, arrangements, parts and combinations, are set forth in the appended claims.

We claim:

1. A tongue scraper comprising:

an elongated, molded and unitary handle having a central longitudinal axis;

a body including a blade having a pair of ends and a mid-section therebetween with a curve therein such that the ends are proximate each other, the mid-section therebetween defined by a pair of opposing surfaces on the blade, the ends each being molded within the handle in a substantially planar manner with each other while the mid-section of the blade including a twist such that the opposing surfaces are non-planar with the ends as molded in the handle; and wherein the mid-section is bent at an angle of at least 20 degrees perpendicular to the central longitudinal axis.

2. The tongue scraper of claim 1 wherein the body is of a substantially tear-drop shape.

3. The tongue scraper of claim 1 wherein the mid-section is twisted at least 45° from either end.

4. The tongue scraper of claim 1 wherein the mid-section is twisted at least 70° from either end.

5. The tongue scraper of claim 1 wherein the mid-section is twisted 90° from either end.

6. A tongue scraper comprising:

a handle having a central longitudinal axis therein;

a blade connected to said handle; said blade having a pair of ends, said ends being adjacent and substantially tangential to said central longitudinal axis;

said blade further including a pair of mid-portions, each mid-portion extending from one of said ends, said mid-portions being connected by an arcuate end; said arcuate end substantially lying in a reference plane, said reference plane intersecting said central longitudinal axis, and each of said mid-portions being twisted between 1° and 179°; and wherein the mid-section is bent at an angle of at least 20 degrees perpendicular to the central longitudinal axis.

7. The tongue scraper of claim 6 wherein the ends are planar with each other.

8. The tongue scraper of claim 7 wherein the ends are planar with each other and the central longitudinal axis.

9. The tongue scraper of claim 8 wherein the reference plane is 70° from the planar ends.

* * * * *